(12) United States Patent
Yu et al.

(10) Patent No.: US 12,257,083 B2
(45) Date of Patent: Mar. 25, 2025

(54) METHODS FOR SATURATION CORRECTION AND DYNAMIC GAIN CONFIGURATION AND APPARATUSES FOR PERFORMING THE SAME

(71) Applicant: Accuray Inc., Sunnyvale, CA (US)

(72) Inventors: Zhicong Yu, Highland Hts., OH (US); Amit Jain, Solon, OH (US); Daniel Gagnon, Twinsburg, OH (US); Chuanyong Bai, Solon, OH (US); Marc Chappo, Elyria, OH (US)

(73) Assignee: Accuray Inc., Sunnyvale, CA (US)

( * ) Notice: Subject to any disclaimer, the term of this patent is extended or adjusted under 35 U.S.C. 154(b) by 353 days.

(21) Appl. No.: 17/666,129

(22) Filed: Feb. 7, 2022

(65) Prior Publication Data
US 2023/0248329 A1    Aug. 10, 2023

(51) Int. Cl.
*A61B 6/03* (2006.01)
*A61B 6/00* (2006.01)
*A61B 6/58* (2024.01)
*G01T 1/17* (2006.01)

(52) U.S. Cl.
CPC .............. *A61B 6/032* (2013.01); *A61B 6/482* (2013.01); *A61B 6/5205* (2013.01); *A61B 6/5258* (2013.01); *A61B 6/542* (2013.01); *A61B 6/585* (2013.01); *G01T 1/17* (2013.01)

(58) Field of Classification Search
None
See application file for complete search history.

(56) References Cited

U.S. PATENT DOCUMENTS

| 4,190,773 | A  | 2/1980  | Braden et al.   |
| 5,615,279 | A  | 3/1997  | Yoshioka et al. |
| 6,233,478 | B1 | 5/2001  | Liu             |
| 6,307,909 | B1 | 10/2001 | Flohr et al.    |

(Continued)

FOREIGN PATENT DOCUMENTS

| CN | 1271261 A | 10/2000 |
| CN | 1947154 A | 4/2007  |

(Continued)

OTHER PUBLICATIONS

Notice of Allowance from U.S. Appl. No. 17/479,645 dated Sep. 27, 2023, 78 pages.

(Continued)

*Primary Examiner* — Thomas R Artman
(74) *Attorney, Agent, or Firm* — Calfee, Halter & Griswold LLP (57) ABSTRACT

Saturation in at least one saturated ray is in a method including identifying a saturated ray corresponding to a first ray of a radiation source received at a radiation detector after passing through a reference point during a current view of the radiation detector, identifying at least one non-saturated ray corresponding to a second ray of the radiation source received at the radiation detector, and responsive to the identifying, adjusting a value for the saturated ray based on a value of the at least one non-saturated ray. The non-saturated ray can be a ray from an adjacent view of a current rotation, an adjacent view of a previous or subsequent rotation, or a conjugate ray. Methods of selecting a gain level to avoid saturation are also disclosed.

11 Claims, 7 Drawing Sheets

(56) References Cited

U.S. PATENT DOCUMENTS

| | | | |
|---|---|---|---|
| 7,050,528 B2 | 5/2006 | Chen | |
| 7,108,421 B2 | 9/2006 | Gregerson et al. | |
| 7,209,537 B2 * | 4/2007 | Popescu | A61B 6/482 |
| | | | 378/108 |
| 7,272,429 B2 * | 9/2007 | Walker | A61B 6/4085 |
| | | | 600/407 |
| 7,302,038 B2 | 11/2007 | Mackie et al. | |
| 7,336,759 B2 | 2/2008 | Nukui | |
| 7,433,443 B1 | 10/2008 | Tkaczyk et al. | |
| 7,453,976 B1 | 11/2008 | Yin | |
| 7,649,974 B2 * | 1/2010 | Arenson | A61B 6/583 |
| | | | 378/5 |
| 7,660,380 B2 | 2/2010 | Boese et al. | |
| 7,829,860 B2 * | 11/2010 | Nygard | G01T 1/20186 |
| | | | 250/366 |
| 8,116,430 B1 | 2/2012 | Shapiro et al. | |
| 8,199,873 B2 * | 6/2012 | Star-Lack | G06T 11/005 |
| | | | 378/7 |
| 8,395,126 B2 * | 3/2013 | Takahashi | H04N 5/32 |
| | | | 250/252.1 |
| 8,467,497 B2 | 6/2013 | Lu et al. | |
| 8,588,363 B2 | 11/2013 | Flohr | |
| 9,247,919 B2 * | 2/2016 | Goshen | A61B 6/52 |
| 9,400,332 B2 | 7/2016 | Star-Lack et al. | |
| 9,952,164 B2 | 4/2018 | Wiedmann et al. | |
| 10,176,601 B2 * | 1/2019 | Morf | G01T 1/247 |
| 11,337,668 B2 | 5/2022 | Yu et al. | |
| 2003/0007601 A1 | 1/2003 | Jaffray et al. | |
| 2003/0076927 A1 | 4/2003 | Nakashima et al. | |
| 2004/0068169 A1 | 4/2004 | Mansfield et al. | |
| 2004/0091079 A1 | 5/2004 | Zapalac | |
| 2004/0102688 A1 | 5/2004 | Walker et al. | |
| 2004/0202360 A1 | 10/2004 | Besson | |
| 2005/0053188 A1 | 3/2005 | Gohno | |
| 2005/0251029 A1 | 11/2005 | Khamene et al. | |
| 2006/0104496 A1 | 5/2006 | Arenson et al. | |
| 2006/0109951 A1 * | 5/2006 | Popescu | A61B 6/032 |
| | | | 378/4 |
| 2006/0109954 A1 | 5/2006 | Gohno | |
| 2006/0262894 A1 | 11/2006 | Bernhardt et al. | |
| 2007/0127621 A1 | 6/2007 | Grass et al. | |
| 2007/0189444 A1 | 8/2007 | Van Steven-Daal et al. | |
| 2007/0237288 A1 | 10/2007 | Tkaczyk et al. | |
| 2008/0099689 A1 * | 5/2008 | Nygard | G01T 1/17 |
| | | | 250/370.09 |
| 2008/0103834 A1 | 5/2008 | Reiner | |
| 2008/0112532 A1 | 5/2008 | Schlomka | |
| 2009/0080603 A1 | 3/2009 | Shukla et al. | |
| 2009/0135994 A1 | 5/2009 | Yu et al. | |
| 2009/0161826 A1 | 6/2009 | Gertner et al. | |
| 2009/0225932 A1 | 9/2009 | Zhu et al. | |
| 2009/0283682 A1 | 11/2009 | Star-Lack et al. | |
| 2009/0304142 A1 | 12/2009 | Ruimi et al. | |
| 2010/0046819 A1 | 2/2010 | Noo et al. | |
| 2010/0142791 A1 | 6/2010 | Tsuji | |
| 2010/0208964 A1 | 8/2010 | Wiegert et al. | |
| 2011/0060566 A1 | 3/2011 | Bertram et al. | |
| 2011/0142312 A1 | 6/2011 | Toth et al. | |
| 2011/0176717 A1 | 7/2011 | Siren et al. | |
| 2011/0255656 A1 | 10/2011 | Star-Lack et al. | |
| 2011/0255657 A1 | 10/2011 | Noordhoek | |
| 2012/0014582 A1 | 1/2012 | Schaefer et al. | |
| 2012/0018646 A1 * | 1/2012 | Takahashi | H04N 5/32 |
| | | | 250/371 |
| 2012/0121157 A1 | 5/2012 | Irie et al. | |
| 2012/0207370 A1 | 8/2012 | Fahimian et al. | |
| 2012/0263360 A1 | 10/2012 | Zhu et al. | |
| 2012/0294504 A1 | 11/2012 | Kyriakou | |
| 2013/0004052 A1 | 1/2013 | Chen et al. | |
| 2013/0101082 A1 | 4/2013 | Jordan et al. | |
| 2013/0294570 A1 | 11/2013 | Hansis | |
| 2013/0308745 A1 * | 11/2013 | Goshen | G06T 11/005 |
| | | | 378/5 |
| 2013/0343515 A1 | 12/2013 | Besson | |
| 2014/0018671 A1 | 1/2014 | Li et al. | |
| 2014/0086383 A1 | 3/2014 | Huwer et al. | |
| 2014/0105352 A1 | 4/2014 | Williams | |
| 2014/0110594 A1 | 4/2014 | Star-Lack et al. | |
| 2014/0169652 A1 | 6/2014 | Vic et al. | |
| 2014/0177786 A1 * | 6/2014 | Wiedmann | G01N 23/083 |
| | | | 378/19 |
| 2014/0247919 A1 | 9/2014 | Zhang et al. | |
| 2015/0297165 A1 | 10/2015 | Tanaka et al. | |
| 2015/0305696 A1 | 10/2015 | Yamakawa et al. | |
| 2016/0005194 A1 | 1/2016 | Schretter et al. | |
| 2016/0016009 A1 | 1/2016 | Manzke et al. | |
| 2016/0120486 A1 | 5/2016 | Goto et al. | |
| 2016/0220844 A1 | 8/2016 | Paysan et al. | |
| 2016/0262709 A1 | 9/2016 | Siewerdsen et al. | |
| 2017/0000428 A1 | 1/2017 | Goto | |
| 2017/0197098 A1 | 7/2017 | Hirasawa et al. | |
| 2017/0205360 A1 | 7/2017 | Cinquin et al. | |
| 2017/0278277 A1 | 9/2017 | Morf et al. | |
| 2017/0332982 A1 | 11/2017 | Koehler et al. | |
| 2018/0028143 A1 | 2/2018 | Wiggers et al. | |
| 2018/0070894 A1 | 3/2018 | Osaki et al. | |
| 2018/0144510 A1 | 5/2018 | Lachaine | |
| 2018/0192978 A1 | 7/2018 | Naylor et al. | |
| 2018/0345042 A1 | 12/2018 | Voronenko et al. | |
| 2019/0099149 A1 | 4/2019 | Li | |
| 2020/0016432 A1 | 1/2020 | Maolinbay | |
| 2020/0121267 A1 | 4/2020 | Deutschmann | |
| 2020/0170590 A1 | 6/2020 | Gagnon et al. | |
| 2020/0402644 A1 | 12/2020 | Zhou et al. | |
| 2021/0165122 A1 | 6/2021 | Morton | |
| 2023/0248329 A1 * | 8/2023 | Yu | A61B 6/482 |
| | | | 378/4 |

FOREIGN PATENT DOCUMENTS

| | | | |
|---|---|---|---|
| CN | 101466313 A | 6/2009 | |
| CN | 102711617 A | 10/2012 | |
| CN | 103339657 A | 10/2013 | |
| CN | 103690184 A | 4/2014 | |
| DE | 102006007058 A1 | 7/2007 | |
| DE | 102012200150 A1 | 7/2013 | |
| EP | 1062914 A1 | 12/2000 | |
| EP | 2383702 A1 | 11/2011 | |
| JP | H08252248 A | 10/1996 | |
| JP | 09218939 A | 8/1997 | |
| JP | H105210 A | 1/1998 | |
| JP | 2004000356 A | 1/2004 | |
| JP | 2004136021 A | 5/2004 | |
| JP | 2005080919 A | 5/2004 | |
| JP | 2004223255 A | 8/2004 | |
| JP | 2004530467 A | 10/2004 | |
| JP | 2006122679 A | 5/2006 | |
| JP | 2006141999 A | 6/2006 | |
| JP | 2006239003 A | 9/2006 | |
| JP | 2008036275 A | 2/2008 | |
| JP | 2008544831 A | 12/2008 | |
| JP | 2009533086 A | 9/2009 | |
| JP | 2009297314 A | 12/2009 | |
| JP | 2010284325 A | 12/2010 | |
| JP | 2011067555 A | 4/2011 | |
| JP | 2012024145 A | 2/2012 | |
| JP | 2014503332 A | 2/2014 | |
| JP | 2014511186 A | 5/2014 | |
| JP | 2014528767 A | 10/2014 | |
| JP | 2017131496 A | 8/2017 | |
| JP | 2017185219 A | 10/2017 | |
| JP | 2017531228 A | 10/2017 | |
| WO | 2005112753 A2 | 12/2005 | |
| WO | 2006078386 A2 | 7/2006 | |
| WO | 2010014288 A1 | 2/2010 | |
| WO | WO-2010070583 A1 * | 6/2010 | A61B 6/032 |
| WO | 2010099621 A1 | 9/2010 | |
| WO | 2015103184 A1 | 7/2015 | |
| WO | 2017104700 A1 | 6/2017 | |

(56) References Cited

FOREIGN PATENT DOCUMENTS

| WO | 2018156968 A1 | 8/2018 |
|----|---------------|--------|
| WO | 2018183748 A1 | 10/2018 |

OTHER PUBLICATIONS

Office Action from Chinese Application No. 201980078487.6 dated Mar. 1, 2024, 29 pages.
Office Action from Japanese Application No. 2021-521751 dated Feb. 7, 2024, 8 pages.
Notice of Allowance from U.S. Appl. No. 17/383,740 dated Mar. 15, 2023, 11 pages.
Office Action from Japanese Application No. 2021-521849 dated Sep. 26, 2023, 16 pages.
Office Action from Japanese Application No. 2021-531088 dated Sep. 26, 2023, 14 pages.
Office Action from Japanese Application No. 2021-521757 dated Oct. 3, 2023, 18 pages.
Office Action from Japanese Application No. 2021-521751 dated Aug. 29, 2023, 5 pages.
Office Action from Japanese Application No. 2021-521845 dated Aug. 29, 2023, 4 pages.
Schäfer, et al., FBP and BPF reconstruction methods for circular X-ray tomography with off-center detector, Med. Phys., Jul. 2011, pp. S85-S94, vol. 38, No. 7.
Siewerdsen, et al., A simple, direct method for x-ray scatter estimation and correction in digital radiography and cone-beam CT, Med. Phys., Jan. 2006, pp. 187-197, vol. 33, No. 1.
Spearman, et al., Effect of Automated Attenuation-based Tube Voltage Selection on Radiation Dose at CT: An Observational Study on a Global Scale, Radiology, Apr. 2016, pp. 167-174, vol. 279, No. 1.
Sun, et al., Improved scatter correction using adaptive scatter kernel superposition, Physics in Medicine and Biology, Oct. 2010, pp. 6695-6720, vol. 55.
Tang, et al., A sinogram extrapolation method for CT field of view extension, Proceedings of the Fifth CT Meeting, 2018, pp. 206-209.
Wang, et al., A General Cone-Beam Reconstruction Algorithm, IEEE Transactions on Medical Imaging, Sep. 1993, pp. 486-496, vol. 12, No. 3.
Wang, Ge, X-Ray micro-CT with a displaced detector array, Medical Physics, Jul. 2002, pp. 1634-1636, vol. 29, No. 7.
Wertz, et al., Fast kilovoltage/megavoltage (kVMV) breathhold cone-beam CT for image-guided radiotherapy of lung cancer, Physics in Medicine and Biology, 2010, pp. 4203-4217, vol. 55.
Wu, et al., Metal artifact correction for x-ray computed tomography using kV and selective MV imaging, Medical Physics, Dec. 2014, pp. 121910-1-121910-15, vol. 41, No. 12.
Yang, et al., Scattering estimation for cone-Beam CT Using Local Measurement Based on Compressed Sensing, IEEE transactions on Nuclear Science, Mar. 2018, pp. 941-949, vol. 65, No. 3.
Yu, et al., Radiation dose reduction in computed tomography: techniques and future perspective, Imaging Med., Oct. 2009, pp. 65-84, vol. 1.
Zamyatin, et al., Helical cone beam CT with an asymmetrical detector, Medical Physics, Oct. 2005, pp. 3117-3127, vol. 32, No. 10.
Zbijewski, et al., Efficient Monte Carlo Based Scatter Artifact Reduction in Cone-Beam Micro-CT, IEEE Transactions on Medical Imaging, Jul. 2006, pp. 817-827, vol. 25, No. 7.
Zhu, et al., Scatter Correction Method for X-ray CT Using Primary Modulation: Theory and Preliminary Results, IEEE Transactions on Medical Imaging, Dec. 2006, pp. 1573-1587, vol. 25, No. 12.
Zhu, et al. Noise suppression in scatter correction for cone-beam CT, American Association of Physicists in Medicine, 2009, pp. 741-752, vol. 36, No. 3.
Invitation to Pay Additional Fees from PCT/US2022/035500 dated Oct. 13, 2022, 14 pages.
Alvarez, et al., Energy-selective Reconstructions in X-ray Computerized Tomography, Physics in Medicine and Biology, 1976, pp. 733-744, vol. 21, No. 5.
Anas, et al., High-quality 3D correction of ring and radiant artifacts in flat panel detector-based cone beam volume CT imaging, Phys. Med. Biol., 2011, pp. 6495-6519, vol. 56.
Bootsma, et al., Spatial frequency spectrum of the x-ray scatter distribution in CBCT projections, Med. Phys., Nov. 2013, pp. 111901-1-111901-15, vol. 40, No. 11.
Clackdoyle, et al., Data consistency conditions for truncated fanbeam and parallel projections, Med. Phys. Feb. 2015, pp. 831-845, vol. 42, No. 2.
Defrise, et al., A solution to the long-object problem in helical cone-beam tomography, Physics in Medicine and Biology, 2000, pp. 623-643, vol. 45.
Hsieh, et al., A novel reconstruction algorithm to extend the CT scan field-of-view, Med. Phys., Sep. 2004, pp. 2385-2391, vol. 31, No. 9.
International Search Report and Written Opinion from PCT/US2019/063071 dated Mar. 18, 2020.
International Search Report and Written Opinion from PCT/US2019/063073 dated Apr. 3, 2020.
International Search Report and Written Opinion from PCT/US2019/063074 dated Mar. 23, 2020.
International Search Report and Written Opinion from PCT/US2019/063076 dated Mar. 16, 2020.
International Search Report and Written Opinion from PCT/US2019/063077 dated Mar. 16, 2020.
International Search Report and Written Opinion from PCT/US2019/063078 dated Oct. 8, 2020.
International Search Report and Written Opinion from PCT/US2019/063080 dated Mar. 16, 2020.
International Search Report and Written Opinion from PCT/US2019/063083 dated Mar. 16, 2020.
International Search Report and Written Opinion from PCT/US2019/063085 dated Mar. 16, 2020.
International Search Report and Written Opinion from PCT/US2019/063086 dated Nov. 16, 2020.
International Search Report and Written Opinion from PCT/US2019/063087 dated Apr. 3, 2020.
International Search Report and Written Opinion from PCT/US2021/039824 dated Mar. 4, 2022.
International Search Report and Written Opinion from PCT/US2021/042906 dated Mar. 21, 2022.
Invitation to Pay Additional Fees from PCT/US2019/063086 dated Mar. 26, 2020.
Jeon, et al., Generation of hybrid sinograms for the recovery of kV-CT images with metal artifacts for helical tomotherapy.
Johnson, Thorsten, Dual-Energy CT: General Principles, American Journal of Roentgenology, Nov. 2012, pp. S3-S8, vol. 199.
Kang, et al., Accurate positioning for head and neck cancer patients using 2D and 3D image guidance, Journal of Applied Clinical Medical Physics, Mar. 2011, pp. 1-14, vol. 12, No. 1.
Katsevich, A., An improved exact filtered backprojection algorithm for spiral computed tomography, Advances in Applied Mathematics, 2004, pp. 691-697, vol. 32.
Kudo, et al., Exact and approximate algorithms for helical cone-beam CT, Physics in Medicine and Biology, 2004, pp. 1-26, vol. 49, No. 13.
Kunze, et al., Cone beam reconstruction with displaced flat panel detector, 10th International Meeting on Fully Three-Dimensional Image Reconstruction in Radiology and Nuclear Medicine, 2009, pp. 138-141.
Li, et al., Scatter kernel estimation with an edge-spread function method for cone-beam computed tomography imaging, Physics in Medicine and Biology, pp. 6729-6748, vol. 51.
Lindsay, et al., Investigation of combined kV/MV CBCT imaging with a high-DQE MV detector, Med. Phys., Feb. 2019, pp. 563-575, vol. 46, No. 2.
Liu, et al., X-Ray micro-CT with a displaced detector array: Application to helical cone-beam reconstruction, Medical Physics, Oct. 2003, pp. 2758-2761, vol. 30, No. 10.

(56) References Cited

OTHER PUBLICATIONS

Maslowski, et al., Acuros CTS: A fast, linear Boltzmann transport equation solver for computed tomography scatter—Part I: Core algorithms and validation, Med. Phys., 2018, pp. 1-15.
Myronakis, et al., Spectral imaging using clinical megavoltage beams and a novel multi-layer imager, Physics in Medicine and Biology, Nov. 2018, pp. 9127-9139, vol. 62, No. 23.
Ning, et al., X-ray scatter correction algorithm for cone beam CT imaging, Med. Phys., May 2004, pp. 1195-1202, vol. 31, No. 5.
Noo, et al., A new scheme for view-dependent data differentiation in fan-beam and cone-beam computed tomography, Physics in Medicine and Biology, 2007, pp. 5593-5414, vol. 52.
Notice of Allowance from U.S. Appl. No. 16/694,190 dated Jun. 23, 2021, 8 pages.
Office Action from U.S. Appl. No. 16/694,202 dated Apr. 9, 2021, 12 pages.
Office Action from U.S. Appl. No. 16/694,145 dated Mar. 17, 2021, 10 pages.
Office Action from U.S. Appl. No. 16/694,190 dated Mar. 26, 2021, 9 pages.
Office Action from U.S. Appl. No. 16/694,192 dated Jun. 10, 2021, 10 pages.
Office Action from U.S. Appl. No. 16/694,218 dated Apr. 15, 2021, 7 pages.
Office Action from U.S. Appl. No. 16/694,161 dated Sep. 13, 2021, 18 pages.
Office Action from U.S. Appl. No. 16/694,230 dated Apr. 1, 2021, 6 pages.
Pearson, et al., Dual-energy (MV/kV) CT with probabilistic attenuation mapping for IGRT applications, Physics of Medical Imaging, 2015, pp. 1-9, vol. 9412.
Ramamurthi, et al., Region of Interest Cone Beam Tomography With Prior CT Data, Conference Record of the 37th Asilomar Conference on Signals, Systems, & Computers, Nov. 2003, pp. 1924-1927, vol. 2.
Restriction Requirement from U.S. Appl. No. 16/694,210 dated Jun. 10, 2021, 6 pages.
Rührnschopf, et al., A general framework and review of scatter correction methods in cone beam CT. Part 2: Scatter estimation approaches, Med. Phys. Sep. 2011, pp. 5186-5199, vol. 38, No. 9.
Schäfer, et al., Cone-beam filtered back-projection for circular X-ray tomography with off-center detector, 10th International Meeting on Fully Three-Dimensional Image Reconstruction in Radiology and Nuclear Medicine, 2009, pp. 86-89.
Office Action from Japanese Application No. 2021-521836 dated Aug. 15, 2023, 19 pages.
European Search Report from EP 23155102.9 dated Jul. 4, 2023.
Office Action from European Application No. 19824059.0 dated Jul. 18, 2023, 4 pages.
Office Action from European Application No. 19824061.6 dated Jul. 24, 2023, 4 pages.
Office Action from Japanese Application No. 2021-531086 dated Jul. 11, 2023, 3 pages.
Office Action from Japanese Application No. 2021-531085 dated Jul. 25, 2023, 8 pages.
Office Action from Japanese Application No. 2021-531084 dated Jul. 25, 2023, 8 pages.
Office Action from Japanese Application No. 2021-531088 dated Mar. 26, 2024, 12 pages.
Cho, et al., Cone-Beam CT From Width-Truncated Projections, Computerized Medical Imaging and Graphics, 1996, pp. 1-9, vol. 20, No. 1.
Office Action from Chinese Application No. 201980079186.5 dated Mar. 26, 2024, 20 pages.
Office Action from Chinese Application No. 201980079114.0 dated Mar. 26, 2024, 17 pages.
Office Action from Chinese Application No. 201980078495.0 dated Mar. 25, 2024, 7 pages.
Office Action from Chinese Application No. 201980078496.5 dated Mar. 26, 2024, 26 pages.
Office Action from Chinese Application No. 201980079075.4 dated Apr. 1, 2024, 35 pages.
Office Action from Chinese Application No. 201980079137.1 dated Apr. 2, 2024, 28 pages.
Office Action from Chinese Application No. 201980078473.4 dated Apr. 1, 2024, 23 pages.
Office Action from European Application No. 19824059.0 dated May 3, 2024, 3 pages.
Office Action from European Application No. 19824061.6 dated May 3, 2024, 3 pages.
Office Action from Japanese Application No. 2021-521849 dated Mar. 12, 2024, 13 pages.
Search Report from Chinese Application No. 201980078473.4 dated Apr. 1, 2024, 5 pages.
Search Report from Chinese Application No. 201980078495.0 dated Mar. 25, 2024, 8 pages.
Search Report from Chinese Application No. 201980078496.5 dated Mar. 26, 2024, 5 pages.

* cited by examiner

METHODS FOR SATURATION CORRECTION AND DYNAMIC GAIN CONFIGURATION AND APPARATUSES FOR PERFORMING THE SAME

FIELD OF THE INVENTION

This disclosure relates to imaging utilizing low-energy radiation (e.g., kilovolt (kV)) and high-energy radiation (e.g., megavolt (MV)) in combination for improved imaging, including for computed tomography (CT) scans.

BACKGROUND

In dual-energy CT scanning, radiation beams with different energies are used for scanning. In a kilovolt (kV) switching acquisition protocol, the radiation voltage is rapidly altered between the low-energy (e.g., the 80 kV) and the high-energy (e.g., the 140 kV) in alternating views. The result is near-simultaneous registered dual-energy data that enables decomposition and is capable of generating high quality images.

Various dual-energy CT systems include a flat panel detector that is configured to detect the radiation beams. However, such flat panel detectors can be limited in their dynamic range. For example, a conventional flat panel detector has 16 bits, as compared to 20 or 24 bits typically employed in a CT detector. As a result of the limited dynamic range, the detector may be saturated at low attenuation paths by the high-energy pulse or even by the low energy pulse.

Accordingly, there may be a need for alternative systems and methods for operating a dual-energy CT system to overcome the limited dynamic range of the flat-panel detector.

BRIEF SUMMARY

In a first embodiment, a method for correcting saturation in at least one saturated ray comprises: identifying a saturated ray corresponding to a first ray of a radiation source received at a radiation detector after passing through a reference point during a current view of the radiation detector; identifying at least one non-saturated ray corresponding to a second ray of the radiation source received at the radiation detector after passing through the reference point during a previous view of the radiation detector or a third ray of the radiation source received at the radiation detector after passing through the reference point during a next view of the radiation detector; and responsive to the identifying, adjusting a value for the saturated ray based on a value of the at least one non-saturated ray. Each of the previous view of the radiation detector and the next view of the radiation detector is adjacent to the current view; and the radiation source has a first energy for the current view and a second energy for the previous view and the next view, the second energy being different than the first energy.

In another embodiment, a method for correcting saturation in at least one saturated ray comprises: identifying a saturated ray corresponding to a first ray of a radiation source received at a radiation detector after passing through a reference point during a current view of the radiation detector; identifying at least one non-saturated ray corresponding to a second ray of the radiation source received at the radiation detector after passing through the reference point during a conjugate view; and responsive to the identifying, adjusting a value for the saturated ray based on a value of the at least one non-saturated ray. The second ray is adjacent to a third ray which is rotated 180° with respect to the first ray; and According to another embodiment, a method of operating a dual-energy imaging system comprises: emitting, from a radiation source, a first plurality of photons at a first energy level; receiving at least some of the first plurality of photons at a radiation detector; outputting from the radiation detector a first signal indicative of a first quantity of the at least some of the first plurality of photons received at the radiation detector amplified by a first gain level for the radiation detector; emitting, from the radiation source, a second plurality of photons at a second energy level; receiving at least some of the second plurality of photons at the radiation detector; and outputting from the radiation detector a second signal indicative of a quantity of the at least some of the second plurality of photons received at the radiation detector amplified by a second gain level for the radiation detector. The first gain level and the second gain level are selected to avoid saturation of a first signal corresponding to the first plurality of photons and a second signal corresponding to the second plurality of photons.

Features that are described and/or illustrated with respect to one embodiment may be used in the same way or in a similar way in one or more other embodiments and/or in combination with or instead of the features of the other embodiments.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of this invention. It will be appreciated that illustrated element boundaries (e.g., boxes, groups of boxes, or other shapes) in the figures represent one embodiment of boundaries. In some embodiments, one element may be designed as multiple elements or that multiple elements may be designed as one element. In some embodiments, an element shown as an internal component of another element may be implemented as an external component and vice versa. Furthermore, elements may not be drawn to scale.

DETAILED DESCRIPTION

The following includes definitions of exemplary terms that may be used throughout the disclosure. Both singular and plural forms of all terms fall within each meaning.

"Component," as used herein can be defined as a portion of hardware, a portion of software, or a combination thereof. A portion of hardware can include at least a processor and a portion of memory, wherein the memory includes an instruction to execute. A component may be associated with a device.

Although described in various embodiments as a "dual scan" or "first scan" and "second scan", the image acquisition methodology described herein can include or otherwise make use of a multiple rotation scan, which may be, for example, a continuous scan (e.g., with a helical source trajectory about a central axis together with longitudinal movement of a patient support through a gantry bore), a non-continuous circular stop-and-reverse scan with incremental longitudinal movement of a patient support, step-and-shoot circular scans, etc. Accordingly, the phrase "dual scan," as used herein, refers to scans including multiple rotations, which may be continuous or non-continuous.

"Logic," synonymous with "circuit" as used herein, includes but is not limited to hardware, firmware, software and/or combinations of each to perform a function(s) or an action(s). For example, based on a desired application or needs, logic may include a software-controlled microprocessor, discrete logic such as an application specific integrated circuit (ASIC), or other programmed logic device and/or controller. Logic may also be fully embodied as software.

"Processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software", as used herein, includes but is not limited to one or more computer readable and/or executable instructions that cause a computer, processor, logic, and/or other electronic device to perform functions, actions, and/or behave in a desired manner. The instructions may be embodied in various forms such as routines, algorithms, modules, or programs including separate applications or code from dynamically linked sources or libraries.

While the above exemplary definitions have been provided, it is Applicant's intention that the broadest reasonable interpretation consistent with this specification be used for these and other terms.

According to one or more embodiments, saturation in at least one saturated ray of a current view is corrected by identifying at least one non-saturated ray corresponding to a subsequent ray of a radiation source received at a radiation detector after passing through a reference point and adjusting a value for the saturated ray based on the value of the at least one non-saturated ray. The subsequent ray may be, for example, a ray received at the radiation detector after passing through the reference point during a previous view of the radiation detector, a next view of the radiation detector, or during a conjugate view of the radiation detector, or during a previous or future rotation (at the same or similar angle). In some embodiments, the radiation source has a first energy for the current view and a second energy for the previous view, the next view, or the conjugate view, where the second energy is different from the first energy. Accordingly, data from an adjacent or conjugate view of a non-saturated ray can be used to adjust a value of the saturated ray, enabling a flat panel detector to be used in a dual energy imaging system despite its limited dynamic range.

Moreover, according to one or more embodiments, a gain value of the radiation detector can be switched in conjunction with the switching energy of the radiation source. In embodiments, photons are emitted from a radiation source at a first energy level and at least some of those photons are received at a radiation detector, which outputs a first signal that is indicative of the quantity of received photons amplified by a first gain level. The radiation source emits photons at a second energy level and at least some of those photons are received at the radiation detector, which outputs a second signal that is indicative of the quantity of received photons amplified by a second gain level. The first gain level is lower than the second gain level. In embodiments, the first energy level is lower than the second energy level, such that high energy pulses are detected using a lower gain level as compared to low energy pulses. Accordingly, the gain level of the detector can be dynamically adjusted based on the expected amount of energy to be deposited at the detector, enabling a flat panel detector to be used in a dual energy imaging system despite its limited dynamic range.

Figure 1:
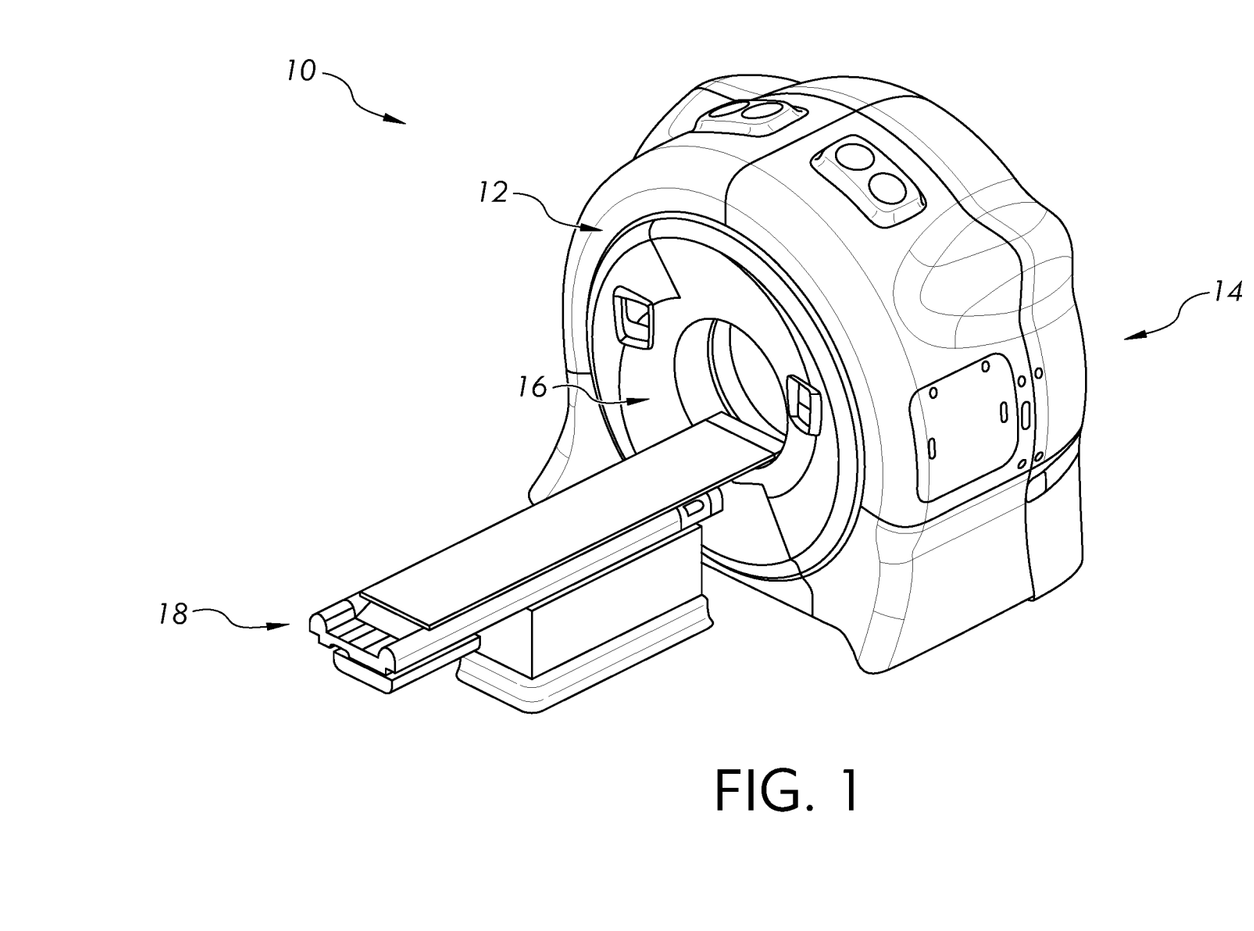
FIG. 1 is an example radiotherapy delivery device according to one or more embodiments described herein.
Figure 2:
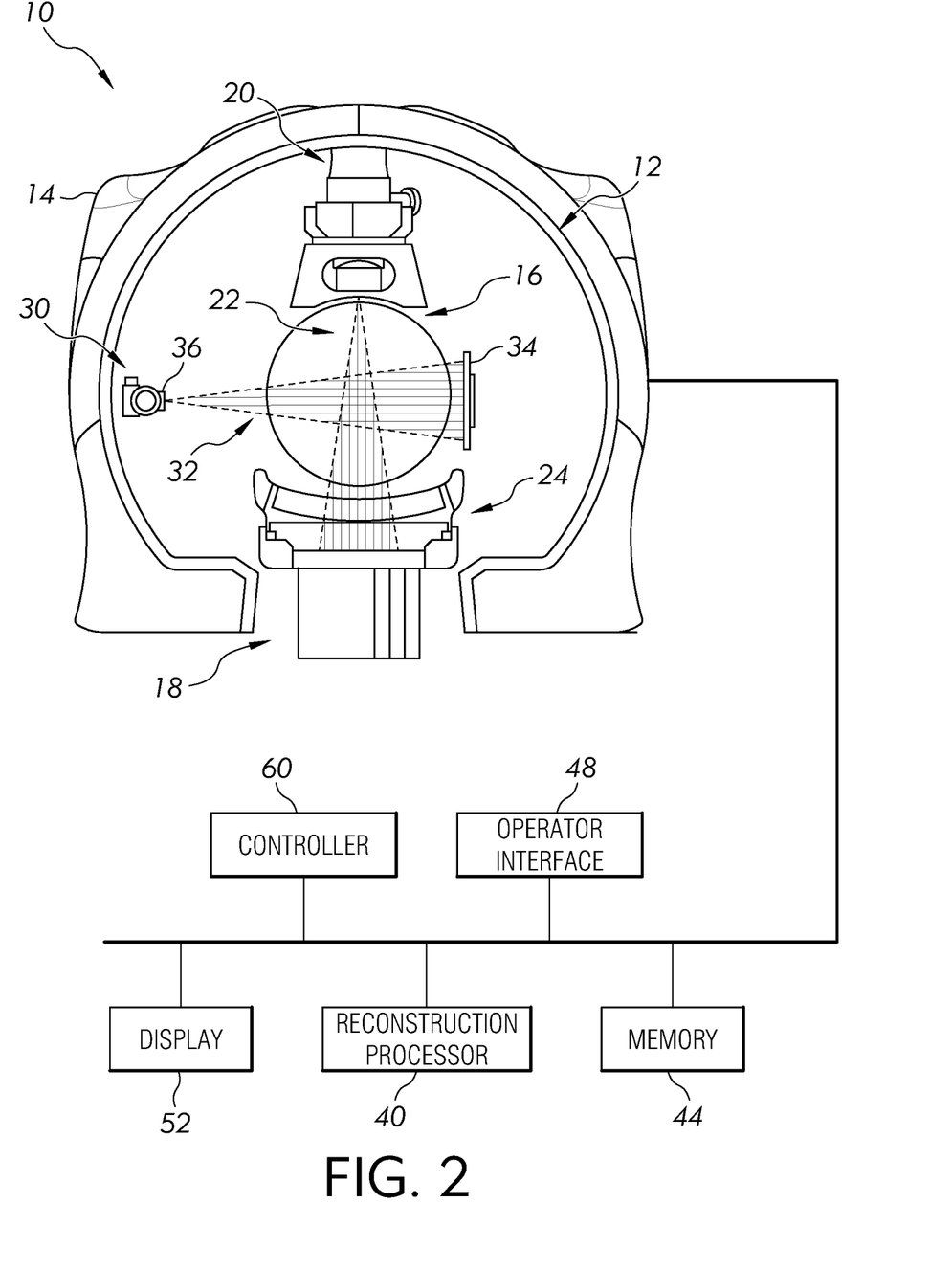
FIG. 2 is an example diagram of a radiotherapy delivery device according to one or more embodiments described herein.

Turning now to FIG. 1 and FIG. 2, a multimodal apparatus 10 is shown. It will be appreciated that the multimodal apparatus 10 may be associated with and/or integrated into a radiotherapy device (as shown in FIG. 2) that can be used for a variety of applications, including, but not limited to IGRT, for example, as an IGRT delivery system. The multimodal apparatus 10 includes a rotatable gantry system, referred to as the gantry 12, supported by or otherwise housed in a support unit or housing 14. The gantry herein refers to a gantry system that comprises one or more gantries (e.g., ring or C-arm) capable of supporting one or more radiation sources and/or associated detectors as they rotate around a target. A rotatable ring gantry 12 may be capable of 10 rpm or more.

The rotatable gantry 12 defines a gantry bore 16 into and through which a patient can be moved and positioned for imaging and/or treatment. In accordance with one embodiment, the rotatable gantry 12 is configured as a slip ring gantry to provide continuous rotation of radiation sources and associated radiation detector(s) while providing sufficient bandwidth for the high-quality imaging data received by the detector(s). A slip-ring gantry can eliminate gantry rotations in alternating directions in order to wind and unwind cables carrying the power and signals associated with the device. Such a configuration will allow for continuous helical computed tomography, including CBCT, even when integrated into an IGRT system.

A patient support 18 is positioned adjacent to the rotatable gantry 12 and configured to support a patient, typically in a horizontal position, for longitudinal movement into and within the rotatable gantry 12. The patient support 18 can move the patient, for example, in a direction perpendicular to the plane of rotation of the gantry 12 (along or parallel to the rotation axis of the gantry 12). The patient support 18 can be operatively coupled to a patient support controller for controlling movement of the patient and patient support 18. The patient support controller can be synchronized with the rotatable gantry 12 and sources of radiation mounted to the rotating gantry for rotation about a patient longitudinal axis in accordance with a commanded imaging and/or treatment plan. The patient support can also be moved in a limited range up and down, left and right once it is in the bore 16 to adjust the patient position for optimal treatment. Axes x, y, and z are shown, where, viewing from the front of the gantry 12, the x-axis is horizontal and points to the right, the y-axis points into the gantry plane, and the z-axis is vertical and points to the top. The x-, y-, and z-axes follow the right-hand rule.

As shown in FIG. 2, the multimodal apparatus 10 includes a radiation source 30 coupled to or otherwise supported by the rotatable gantry 12. In this embodiment, the radiation source 30 is a source of imaging radiation and emits a radiation beam (indicated generally as 32) for generating high-quality images. In this embodiment, the source of imaging radiation is an x-ray source 30, configured as a kilovoltage (kV) source (e.g., a clinical x-ray source having an energy level in the range of about 20 kV to about 150 kV). In one embodiment, the low energy radiation source comprises a kilo-electron volt peak photon energy (keV) up to 150 keV. The imaging radiation source can be any type of transmission source suitable for imaging. For example, the imaging radiation source may be, for example, an x-ray generating source. References herein to x-ray, x-ray imaging, x-ray imaging source, etc. are exemplary for particular embodiments. Other imaging transmission sources can be used interchangeably in various other embodiments.

In various embodiments, the radiation source 30 is rapidly switched between a first voltage (e.g., about 80 kV) and a second voltage (e.g., about 140 kV) between projection views, thereby providing near-simultaneous registered dual-energy data. In embodiments, the voltage of the radiation source 30 is switched from the first voltage to the second voltage between two consecutive projection views such that a current view at the first voltage has a previous adjacent view and a next adjacent view at the second voltage. In embodiments, the voltage of the radiation source 30 is switched according to a pre-determined sequence (e.g., a repeating sequence of three pulses at the first voltage followed by one pulse at the second voltage or the like).

An x-ray detector 34 (e.g., two-dimensional flat detector) is coupled to or otherwise supported by the rotatable gantry 12. The x-ray detector 34 is positioned to receive radiation from the x-ray source 30 and can rotate along with the x-ray source 30. It will be appreciated that the x-ray detector 34 can take on a number of configurations without departing from the scope of the disclosed technology. As illustrated in FIGS. 1 and 2, the x-ray detector 34 can be configured as a flat-panel detector (e.g., a multi-row flat panel detector). The detector 34 can detect or otherwise measure the amount of radiation not attenuated and therefore infer what was in fact attenuated by the patient or associated patient ROI (by comparison to what was initially generated). The detector 34 can detect or otherwise collect attenuation data from different angles as the radiation source 30 rotates around and emits radiation toward the patient.

Although FIGS. 1 and 2 depict a multimodal apparatus 10 with a radiation source 30 mounted to a ring gantry 12, other embodiments may include other types of rotatable imaging apparatuses, including, for example, C-arm gantries and robotic arm-based systems. In gantry-based systems, a gantry rotates the imaging radiation source 30 around an axis passing through the isocenter. Gantry-based systems include C-arm gantries, in which the imaging radiation source 30 is mounted, in a cantilever-like manner, over and rotates about the axis passing through the isocenter. Gantry-based systems further include ring gantries, for example, rotatable gantry 12, having generally toroidal shapes in which the patient's body extends through a bore of the ring/toroid, and the imaging radiation source 30 is mounted on the perimeter of the ring and rotates about the axis passing through the isocenter. In some embodiments, the gantry 12 rotates continuously. In other embodiments, the gantry 12 utilizes a cable-based system that rotates and reverses repeatedly.

A collimator or beamformer assembly (indicated generally as 36) is positioned relative to the x-ray source 30 to selectively control and adjust a shape of a radiation beam 32 emitted by the x-ray source 30 to selectively expose a portion or region of the active area of the x-ray detector 34. The beamformer can also control how the radiation beam 32 is positioned on the x-ray detector 34. In one embodiment, the beamformer 36 could have one degree/dimension of motion (e.g., to make a thinner or fatter slit). In another embodiment, the beamformer 36 can have two degrees/dimensions of motion (e.g., to make various sized rectangles). In other embodiments, the beamformer 36 may be capable of various other dynamically-controlled shapes, including, for example, parallelograms. All of these shapes may be dynamically adjusted during a scan. In some embodiments, blocking portions of the beamformer can be rotated and/or translated.

The beamformer 36 may be configured in a variety of ways that allow it to adjust the shape of the radiation beam 32 emitted by the x-ray source 30. For example, the beamformer 36 can be configured to include a set of jaws or other suitable members that define and selectively adjust the size of an aperture through which the radiation beam from the x-ray source 30 may pass in a collimated manner. In accordance with one exemplary configuration, the beamformer 36 can include an upper jaw and a lower jaw, where the upper and lower jaws are movable in different directions (e.g., parallel directions) to adjust the size of the aperture through which the radiation beam from the x-ray source 30 passes, and also to adjust the beam 32 position relative to the patient to illuminate only the portion of the patient to be imaged for optimized imaging and minimized patient dose.

As shown in FIG. 2, the multimodal apparatus 10 may be integrated with a radiotherapy device that includes a high-energy radiation source (e.g., MV) 20 coupled to or otherwise supported by the rotatable gantry 12. In accordance with one embodiment, the high-energy radiation source 20 is configured as a source of therapeutic radiation, such as a high-energy source of radiation used for treatment of a tumor within a patient in a region of interest. In other embodiments, the high-energy radiation source 20 is also configured as a source of imaging radiation, or at least utilized as such. It will be appreciated that the source of therapeutic radiation can be a high-energy x-ray beam (e.g., MV x-ray beam), and/or a high-energy particle beam (e.g., a beam of electrons, a beam of protons, or a beam of heavier ions, such as carbon) or another suitable form of high-energy radiation. In one embodiment, the high-energy radiation source 20 comprises a mega-electron volt peak photon energy (MeV) of 1 MeV or greater. In one embodiment, the high-energy x-ray beam has an average energy greater than about 0.8 MeV. In another embodiment, the high-energy x-ray beam has an average energy greater than about 0.2 MeV. In another embodiment, the high-energy x-ray beam has an average energy greater than about 150 keV. Generally, the high-energy radiation source 20 has a higher energy level (peak and/or average, etc.) than the low-energy radiation source 30.

In one embodiment, the high-energy radiation source 20 is a LINAC producing therapeutic radiation (e.g., MV) and the imaging system comprises an independent low-energy radiation source 30 producing relatively low intensity and lower energy imaging radiation (e.g., kV). In other embodiments, the therapeutic radiation source 20 could be a radioisotope, such as, for example, Co-60, which can generally have energy of greater than about 1 MeV. The high-energy radiation source 20 can emit one or more beams of radiation (indicated generally by 22) toward a region-of-interest (ROI) within a patient supported on the patient support 18 in accordance with a treatment plan.

In various embodiments, the high-energy radiation source 20 is utilized as a source of therapeutic radiation and a source of imaging radiation. As discussed in detail below, sources of radiation 20, 30 may be used in conjunction with one another to provide higher quality and better utilized images. References to the therapeutic radiation source 20 herein are to distinguish the high-energy radiation source 20 from the low-energy radiation source 30, which may be used only for imaging. However, references to the therapeutic radiation source 20 include embodiments where the therapeutic radiation source 20 (high-energy radiation source) can be utilized for therapy and/or imaging. In other embodiments, at least one additional radiation source can be coupled to the rotatable gantry 12 and operated to acquire projection data at a peak photon energy distinct from the peak photon energies of sources of radiation 20, 30.

The multimodal apparatus 10 can include an operator/user interface 48, where an operator of the apparatus 10 can interact with or otherwise control the apparatus 10 to provide input relating to scan or imaging parameters and the like. The operator interface 48 can include any suitable input devices, such as a keyboard, mouse, voice-activated controller, or the like. The apparatus 10 can also include a display 52 or other human-readable element to provide output to the operator of the apparatus 10. For example, the display 52 can allow the operator to observe reconstructed patient images and other information, such as imaging or scan parameters, related to operation of the apparatus 10.

As shown in FIG. 2, the multimodal apparatus 10 includes a controller (indicated generally as 60) operatively coupled to one or more components of the apparatus 10. The controller 60 controls the overall functioning and operation of apparatus 10, including providing power and timing signals to the x-ray source 30 and/or the therapeutic radiation source 20, gain signals to the detector 34, and a gantry motor controller that controls rotational speed and position of the rotatable gantry 12. It will be appreciated that the controller 60 can encompass one or more of the following: a patient support controller, a gantry controller, a controller coupled to the therapeutic radiation source 20 and/or the x-ray source 30, a beamformer controller, a controller coupled to the detector 24 and/or the x-ray detector 34, and the like. In one embodiment, the controller 60 is a system controller that can control other components, devices, and/or controllers.

In various embodiments, the reconstruction processor 40, the operator interface 48, the display 52, the controller 60 and/or other components may be combined into one or more components or devices.

The apparatus 10 may include various components, logic, and software. In one embodiment, the controller 60 comprises a processor, a memory, and software. By way of example and not limitation, a multimodal apparatus and/or radiotherapy system can include various other devices and components (e.g., gantries, radiation sources, collimators, detectors, controllers, power sources, patient supports, among others) that can implement one or more routines or steps related to imaging and/or IGRT for a specific application, wherein a routine can include imaging, image-based pre-delivery steps, and/or treatment delivery, including respective device settings, configurations, and/or positions (e.g., paths/trajectories), which may be stored in memory. Furthermore, the controller(s) can directly or indirectly control one or more devices and/or components in accordance with one or more routines or processes stored in memory. An example of direct control is the setting of various radiation source or collimator parameters (power, speed, position, timing, modulation, etc.) associated with imaging or treatment. An example of indirect control is the communication of position, path, speed, etc. to a patient support controller or other peripheral device. The hierarchy of the various controllers that may be associated with the apparatus can be arranged in any suitable manner to communicate the appropriate commands and/or information to the desired devices and components.

Moreover, those skilled in the art will appreciate that the systems and methods may be implemented with other computer system configurations. The illustrated aspects of the invention may be practiced in distributed computing environments where certain tasks are performed by local or remote processing devices that are linked through a communications network. For example, in one embodiment, the reconstruction processor 40 may be associated with a separate system. In a distributed computing environment, program modules may be located in both local and remote memory storage devices. For instance, a remote database, a local database, a cloud-computing platform, a cloud database, or a combination thereof can be utilized with apparatus 10.

Multimodal apparatus 10 can utilize an exemplary environment for implementing various aspects of the invention including a computer, wherein the computer includes the controller 60 (e.g., including a processor and a memory, which may be memory 44) and a system bus. The system bus can couple system components including, but not limited to the memory to the processor, and can communicate with other systems, controllers, components, devices, and processors. Memory can include read only memory (ROM), random access memory (RAM), hard drives, flash drives, and any other form of computer readable media. Memory can store various software and data, including routines and parameters, which may comprise, for example, a treatment plan.

The therapeutic radiation source 20 and/or x-ray source 30 can be operatively coupled to a controller 60 configured to control the relative operation of the therapeutic radiation source 20 and the x-ray source 30. For example, the x-ray source 30 can be controlled and operated simultaneously with the therapeutic radiation source 20. In addition, or alternatively, the x-ray source 30 can be controlled and operated sequentially with the therapeutic radiation source 20, depending on the particular treatment and/or imaging plan being implemented. For example, in various embodiments, the radiation sources 20, 30 can be operated such that the measured projection data from the radiation sources 20, 30 are acquired simultaneously (or essentially/nearly (quasi-) simultaneously, e.g., within about 50 ms of each other) or sequentially (e.g., separated by seconds, minutes, etc.).

It will be appreciated that radiation sources 20, 30 and detector(s) 24, 34 can be configured to provide rotation around the patient during an imaging and/or treatment scan in a number of ways. In one embodiment, synchronizing the motion and exposure of the source 20, 30 with the longitudinal motion of the patient support 18 can provide a continuous helical acquisition or scan of a patient image during a procedure. In addition to continuous rotation of the radiation sources 20, 30 and detector(s) 24, 34 (e.g., continuous and constant rotation of the gantry with constant patient motion speed), it will be appreciated that other variations can be employed without departing from the scope of the disclosed technology. For example, the rotatable gantry 12 and patient support can be controlled such that the gantry 12 rotates in a "back-and-forth" manner (e.g., alternating clockwise rotation and counterclockwise rotation) around a patient supported on the patient support (as opposed to continuously, as is described above) as the support is controlled to move (at a constant or variable speed) relative to the rotatable gantry 12. In another embodiment, with successive step-and-shoot circular scans, movement of the patient support 18 in the longitudinal direction (step) alternates with a scanning revolution by the rotatable gantry 12 (shoot) until the desired volume is captured. The multimodal apparatus 10 is capable of volume-based and planar-based imaging acquisitions. For example, in various embodiments, the multimodal apparatus 10 may be used to acquire volume images and/or planar images and execute the associated processing.

Various other types of radiation source and/or patient support movement may be utilized to achieve relative motion of the radiation source and the patient for generation of projection data. Non-continuous motion of the radiation source and/or patient support, continuous but variable/non-constant (including linear and non-linear) movement, speed, and/or trajectories, etc., and combinations thereof may be used, including in combination with the various embodiments of apparatus 10 described above.

In one embodiment, the gantry 12 rotation speed, the patient support 18 speed, the beamformer shape, and/or the detector readout could all be constant during image acquisition. In other embodiments, one or more of these variables could change dynamically during image acquisition and/or treatment.

In other embodiments, these features can be combined with one or more other image-based activities or procedures, including, for example, patient set up, adaptive therapy monitoring, treatment planning, etc.

During image data acquisition, both the source (e.g., source 30) and detector (e.g., 34) move along an angular path as the gantry 12 rotates. Source 36 and detector 34 may move along their respective paths in a synchronized manner. Data is collected at various positions along the angular path, e.g., when the detector 34 is located at positions 303, 305, 307, as shown in FIG. 3.

At each position 303, 305, 307, the detector 34 will spend a period of time to collect an appropriate type of data before advancing to the next view. The data type may be image data I, which is data relating to the traversal of x-ray from source 30 through an object 26 of interest (sometimes referred to herein as the "scanned object"), or background B data, which is data detected by the detector 34 when the source 30 is powered off. Image data I may be, for example, diagnostic data related to a patient. However, other data may be obtained in the context of the present disclosure. Image data I can be reconstructed to form a 3D representation of the patient using tomographic methods. To detect image I data, source 30 must be powered up and emitting x-rays. Although referred to herein as "emitting x-rays," it should be understood that the source 30 emits a stream (e.g., a ray) of photons that together are referred to as an x-ray or a ray.

Figure 3:
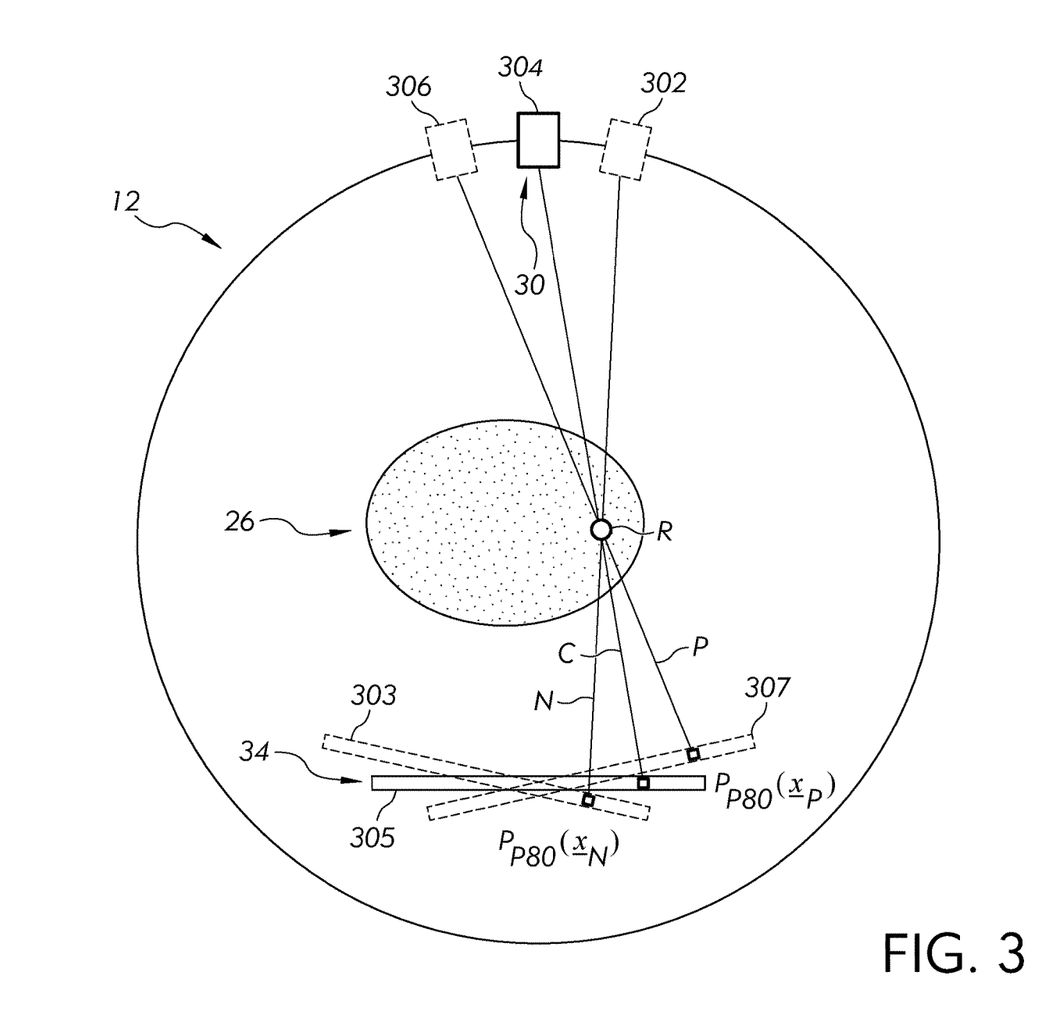
FIG. 3 is an example device configuration in accordance with one or more embodiments described herein.

In embodiments, the radiation source 30 is rapidly switched between a first voltage (e.g., about 140 kV) and a second voltage (e.g., about 80 kV) between projection views, as shown in FIG. 3. In FIG. 3, the position of the radiation source 30 and the x-ray detector 34 in the current view 304 are darkened, while the position of the radiation source 30 and the x-ray detector 34 in the previous and next views are shown in broken lines. In particular, in the previous view, the radiation source is at position 306 and the x-ray detector is at position 307, and in the next view, the radiation source is at position 302 and the x-ray detector is at position 303. Although it should be understood that a plurality of rays are emitted by the radiation source 30 and received by the x-ray detector 34 at each view, a single ray emitted by the radiation source 30 at each position is illustrated in FIG. 3, and additional rays are omitted for clarity. Ray C is emitted during the current view, ray P is emitted during the previous view, and ray N is emitted during the next view.

Each of the illustrated rays C, N, and P passes through a reference point R in the scanned object 26. In the embodiment shown in FIG. 3, the reference point R is located in a peripheral region of the scanned object 26. Although the location of the reference point R is not limited to the peripheral region, it is believed that attenuation of the x-ray by the scanned object is less, making saturation more likely to happen. Accordingly, although the reference point R may be described in various embodiments as being located in a peripheral region, it is contemplated that the reference point R may be located anywhere in the field of view. Each of the rays C, N, and P is received at the radiation detector 34 after passing through the reference point R. In various embodiments, the reference point R is configured as the closest point on the ray to the isocenter.

In the embodiment depicted in FIG. 3, the voltage switching is interleaved, meaning that the emission at one view (e.g., the current view) at the first voltage is followed by an emission at the next view at the second voltage and is preceded by an emission at the previous view at the second voltage. In other words, emissions from the radiation source alternate between the first and second voltages. In various embodiments, saturation correction can be performed on at least one saturated ray using information from non-saturated rays or frames from the current and/or next or previous views. Although saturation correction is described herein as using non-saturated rays, it is contemplated that multiple non-saturated rays from the same frame (i.e., a non-saturated frame) can be used (e.g., averaged) to correct the saturated ray.

Figure 4:
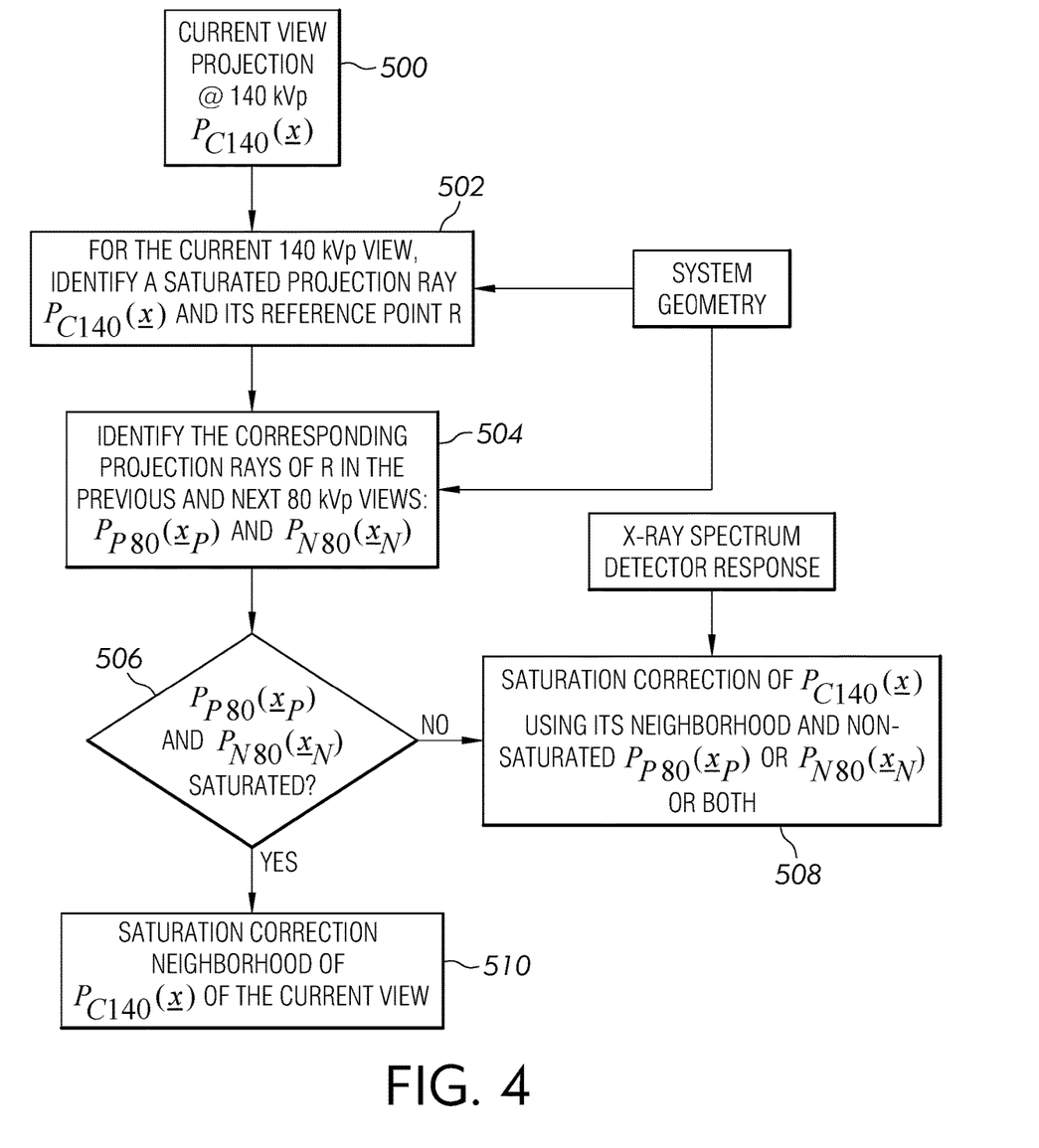
FIG. 4 is a flow chart of an example method of performing saturation correction in saturated rays according to one or more embodiments shown and described herein.

FIG. 4 is a flow chart of an example method of saturation correction using adjacent frames according to various embodiments. In the following description of FIGS. 3 and 4, the current view will be discussed as including an emission at the first voltage (e.g., about 140 kV), and the previous view and the next view will be discussed as including an emission at the second voltage (e.g., about 80 kV). However, it should be understood that, depending on the referenced "current view," the voltages of the current, previous, and next views can be reversed. Moreover, it is contemplated that the non-saturated data can come from one or more non-saturated rays that are neighboring (e.g., adjacent) to the saturated ray in three-dimensional space, whether located during the same rotation or a different rotation, provided that the non-saturated ray has substantially the same path length through the reference point as the saturated ray.

In this example, the amount of energy received by the x-ray detector 34 at position 305 as a result of the ray C (block 500 in FIG. 4) exceeds the dynamic range of the x-ray detector 34. As a result of the receipt of this energy, a controller associated with the x-ray detector 34 determines that the projection ray C is saturated (block 502 in FIG. 4). However, the amount of energy received by the x-ray detector 34 as a result of each of the rays P and N (in this example, approximately one-third of the amount of energy received by the x-ray detector as a result of the ray C) does not exceed the dynamic range of the x-ray detector 34. The controller associated with the x-ray detector 34 identifies the corresponding projection ray from the previous view (e.g., ray P) and the corresponding projection ray from the next view (e.g., ray N) through a reference point R of projection ray C at block 504 in FIG. 4. Based on the amount of energy received by the x-ray detector 34 as a result of ray P and ray N, the controller determines that the projection rays P and N are not saturated (e.g., a "no" at decision block 506). In other words, the controller identifies at least one non-saturated ray from a previous or next view of the x-ray detector.

In various embodiments, the determination of whether a given projection ray is saturated or not can be the result of the controller comparing an output of the x-ray detector in response to the received energy for a given ray to a threshold output value for the x-ray detector. In an embodiment, the controller compares the signal output by the x-ray detector as a result of the receipt of ray C to a maximum signal output value and, upon determining that the signal output by the x-ray detector is equal to the maximum signal output value, the controller determines that the projection ray C is saturated. Furthermore, the controller compares the signal output by the x-ray detector as a result of the receipt of ray P and/or ray N to a maximum signal output value and, upon determining that the signal output by the x-ray detector is less than the maximum signal output value, the controller determines that the corresponding projection ray P or N is not saturated (block 506). In various embodiments, upon determination that the projection rays P and/or N are not saturated (e.g., a "no" at block 506), the data from the corresponding projection rays P and/or N is used to correct the saturated ray of the current ray C (block 508).

In embodiments, while the current ray C is saturated, both of ray P from the previous view and ray N of the next view are not saturated and, accordingly, the saturation correction of ray C can be performed using data from both of ray P and ray N. However, in other embodiments, the current ray C is saturated and one of ray P and ray N is not saturated while the other is saturated. In such embodiments, at block 508, the data from the corresponding projection ray that is not saturated is used for saturation correction while data from the other corresponding projection ray is ignored for the purposes of saturation correction. For example, in embodiments in which the corresponding projection ray P from the previous view is not saturated and the corresponding projection ray N from the next view is saturated, the data from ray P is used for saturation correction while the data from ray N is ignored for saturation correction purposes. As another example, in embodiments in which the corresponding projection ray N from the next view is not saturated and the corresponding projection ray P from the previous view is saturated, the data from ray N is used for saturation correction while the data from ray P is ignored for saturation correction purposes.

In various embodiments, at block 508, neighboring non-saturated projection data is also used for saturation correction in addition to data from any non-saturated data from the adjacent (e.g., previous or next) views. Such neighboring non-saturated projection data can include neighboring non-saturated rays in the same frame or corresponding rays in neighboring non-saturated frames of data. In embodiments, "neighboring" refers to a similar azimuth angle in a consecutive rotation. In embodiments in which both adjacent (e.g., previous or next) views are saturated (e.g., a "yes" at block 506), the neighboring non-saturated projection data is used for saturation correction without data from the adjacent (e.g., previous or next) views (block 510). In embodiments, the controller performs saturation correction using linear or advanced interpolation schemes with the neighboring non-saturated projection data and any non-saturated corresponding projection rays from previous or next views as inputs. The saturation correction performed by the controller is effective to adjust a value for the saturated ray based on a value of the at least one non-saturated ray.

In embodiments in which neighboring non-saturated rays from the same frame as the saturated ray are used for saturation correction, a simple linear interpolation scheme can be employed. One example linear interpolation scheme is averaging the neighboring non-saturated rays (e.g., (ray 1+ray 2)*0.5). In other embodiments, such as when corresponding rays from neighboring non-saturated frames are utilized and the rays are emitted at a different voltage, a spectrum-derived interpolation scheme with scaling can be employed.

When using non-saturated rays from one energy to correct saturated rays from a different energy, the imaging chain and, specifically, the x-ray spectrum, can be considered and the non-saturated measurements can be converted using a correction factor. In one embodiment, a calibrated correction factor is generated by assuming that the projection data in the neighboring non-saturated rays are associated with a particular material (e.g., water). Based on the non-saturated data of this assumed material, together with prior knowledge of the imaging chains (e.g., spectra of both the high energy and low energy emissions), a calibration table can be generated. The neighboring non-saturated rays can then be adjusted based on the values in the calibration table to determine an appropriate value for the saturated ray.

In another embodiment, the correction factor can be calculated using imaging chain information (e.g., spectra) and system geometry with the first pass reconstructed image to virtually generate two projections: one for each of the energies. The correction factor can then be determined and applied to the values of the neighboring non-saturated rays to determine an appropriate value for the saturated ray. In various embodiments, the correction factor determination processes can be performed several times to improve the accuracy of the correction factor.

In the embodiment described in FIGS. 3 and 4, the high and low voltage pulses are interleaved. Accordingly, this ensures that the energy for the current view is different from the energy of the previous and next views. However, in other embodiments, the high and low voltage pulses may or may not be interleaved. Accordingly, in some such embodiments, saturation correction can be performed using conjugate frames instead of adjacent views.

Figure 5:
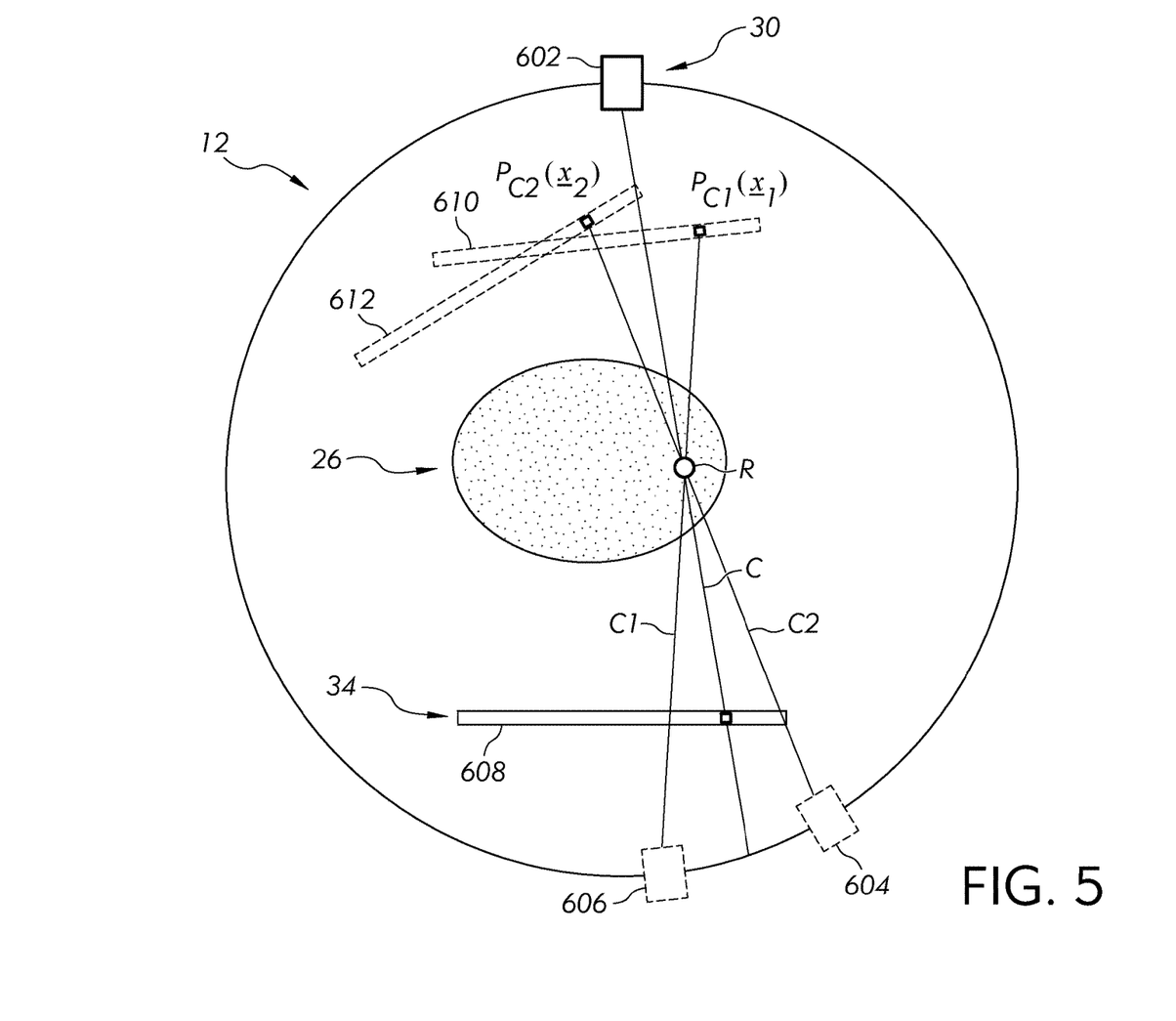
FIG. 5 is another example device configuration in accordance with one or more embodiments described herein

In FIG. 5, the position of the radiation source 30 and the x-ray detector 34 in the current view (602 and 608, respectively) are darkened, while the position of the radiation source 30 and the x-ray detector 34 in the conjugate views are shown in broken lines. In particular, in a first conjugate view, the radiation source is located at position 606 and the x-ray detector is located at position 612, and in a second conjugate view, the radiation source is located at position 604 and the x-ray detector is located at position 610. Although it should be understood that a plurality of rays are emitted by the radiation source 30 and received by the x-ray detector 34 at each view, a single ray emitted by the radiation source 30 at each position is illustrated in FIG. 5, and additional rays are omitted for clarity. Ray C is emitted during the current view and rays C1 and C2 are emitted during the conjugate views.

Each of the illustrated rays C, C1, and C2 passes through a reference point R in the scanned object 26. In the embodiment shown in FIG. 5, the reference point R is located in a peripheral region of the scanned object 26. Each of the rays C, C1, and C2 is received at the radiation detector 34 after passing through the reference point R. In various embodiments, the reference point R is configured as the closest point on the ray to the isocenter.

Figure 6:
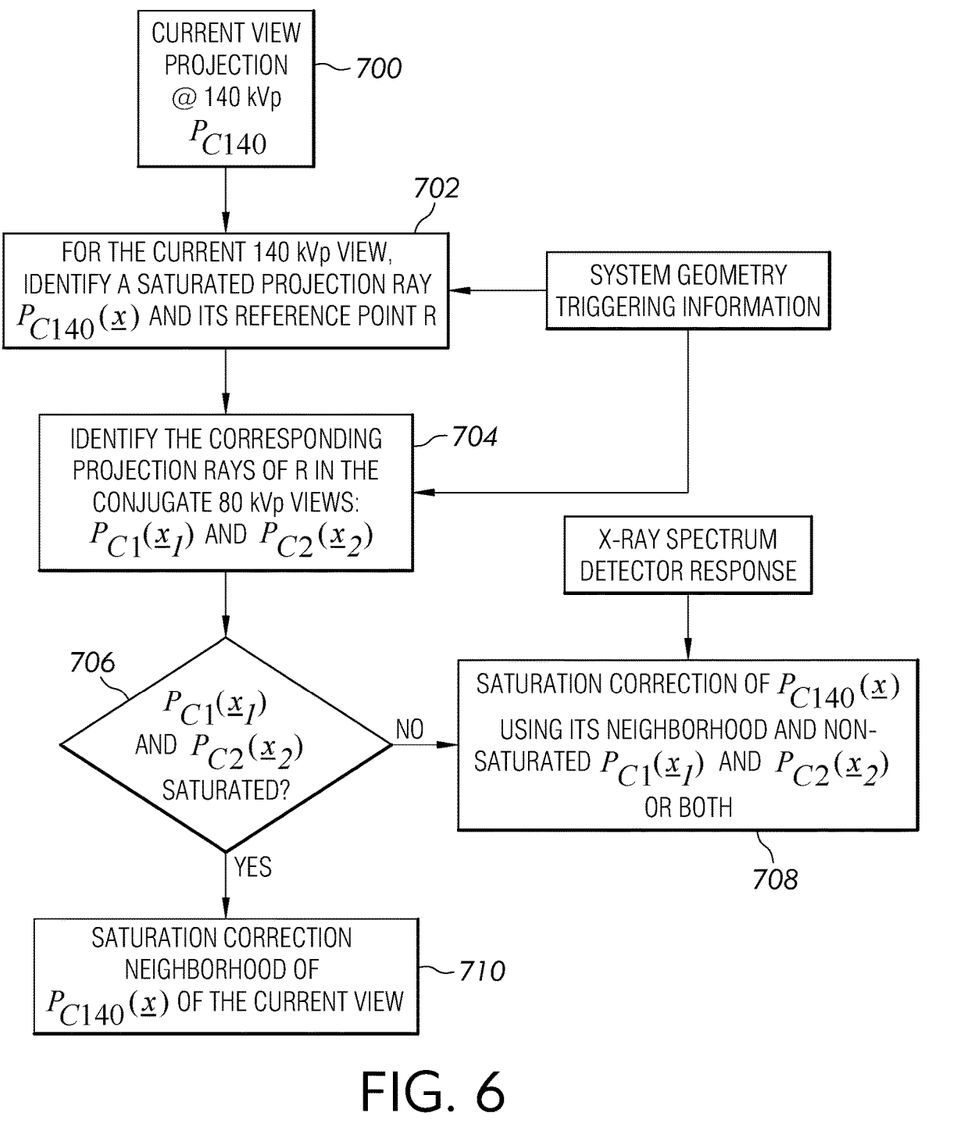
FIG. 6 is a flow chart of another example method of performing saturation correction in saturated rays according to one or more embodiments shown and described herein.

In the embodiment depicted in FIG. 5, the voltage switching may or may not be interleaved. However, the emission at the conjugate views is different from the emission at the current view. The pulse width and tube current remain the same between the current and conjugate views. FIG. 6 is a flow chart of an example method of saturation correction using conjugate frames according to various embodiments. In the following description of FIGS. 5 and 6, the current view will be discussed as including an emission at the first voltage (e.g., about 140 kV), and the conjugate views will be discussed as including an emission at the second voltage (e.g., about 80 kV). However, it should be understood that, depending on the referenced "current view," the voltages of the current and conjugate views can be reversed.

In this example, the amount of energy received by the x-ray detector 34 as a result of the ray C (block 700 in FIG. 6) exceeds the dynamic range of the x-ray detector 34. As a result of the receipt of this energy, a controller associated with the x-ray detector 34 determines that the ray corresponding to projection ray C is saturated (block 702 in FIG. 6). However, the amount of energy received by the x-ray detector 34 as a result of each of the conjugate rays C1 and C2 (in this example, approximately one-third of the amount of energy received by the x-ray detector as a result of the ray C) does not exceed the dynamic range of the x-ray detector 34. The controller associated with the x-ray detector 34 identifies the corresponding projection rays from the conjugate views C1 and C2 through a reference point R of projection ray C at block 704 in FIG. 6. In embodiments, corresponding projection rays are identified based on system geometry triggering information, including x-ray source trajectory information and x-ray cone-beam projection geometry (e.g., information regarding how the detector is positioned relative to the source). Based on the amount of energy received by the x-ray detector 34 as a result of rays C1 and C2, the controller determines that the conjugate projection rays C1 and C2 are not saturated (e.g., a "no" at decision block 706). In other words, the controller identifies at least one non-saturated ray.

In various embodiments, the determination of whether a given projection ray is saturated or not can be the result of the controller comparing an output of the x-ray detector in response to the received energy for a given ray to a threshold output value for the x-ray detector. In an embodiment, the controller compares the signal output by the x-ray detector as a result of the receipt of ray C to a maximum signal output value and, upon determining that the signal output by the x-ray detector is equal to the maximum signal output value, the controller determines that the projection ray C is saturated. Furthermore, the controller compares the signal output by the x-ray detector as a result of the receipt of ray C1 and/or ray C2 to a maximum signal output value and, upon determining that the signal output by the x-ray detector is less than the maximum signal output value, the controller determines that the corresponding projection ray C1 or C2 is not saturated (block 606). In various embodiments, upon determination that the projection rays C1 and/or C2 are not saturated (e.g., a "no" at block 706), the data from the corresponding projection rays C1 and/or C2 is used to correct the saturated ray of the current ray C (block 708).

In embodiments, while the current ray C is saturated, both of rays C1 and C2 are not saturated and, accordingly, the saturation correction of ray C can be performed using data from both of conjugate rays C1 and C2. However, in other embodiments, the current ray C is saturated and one of the conjugate rays C1 and C2 is not saturated while the other is saturated. In such embodiments, at block 608, the data from the corresponding projection ray that is not saturated is used for saturation correction while data from the other corresponding projection ray is ignored for the purposes of saturation correction. For example, in embodiments in which the corresponding projection ray C1 is not saturated and the corresponding projection ray C2 is saturated, the data from ray C1 is used for saturation correction while the data from ray C2 is ignored for saturation correction purposes. As another example, in embodiments in which the corresponding projection ray C2 is not saturated and the corresponding projection ray C1 is saturated, the data from ray C2 is used for saturation correction while the data from ray C1 is ignored for saturation correction purposes.

In various embodiments, at block 708, neighboring non-saturated projection data is also used for saturation correction in addition to data from any non-saturated data from the conjugate views. In embodiments in which both conjugate views are saturated (e.g., a "yes" at block 706), the neighboring non-saturated projection data is used for saturation correction without data from the conjugate views (block 710). In embodiments, the controller performs saturation correction using linear or advanced interpolation schemes with the neighboring non-saturated projection data and any non-saturated corresponding projection rays from conjugate views as inputs. The saturation correction performed by the controller is effective to adjust a value for the saturated ray based on a value of the at least one non-saturated ray.

Figure 7:
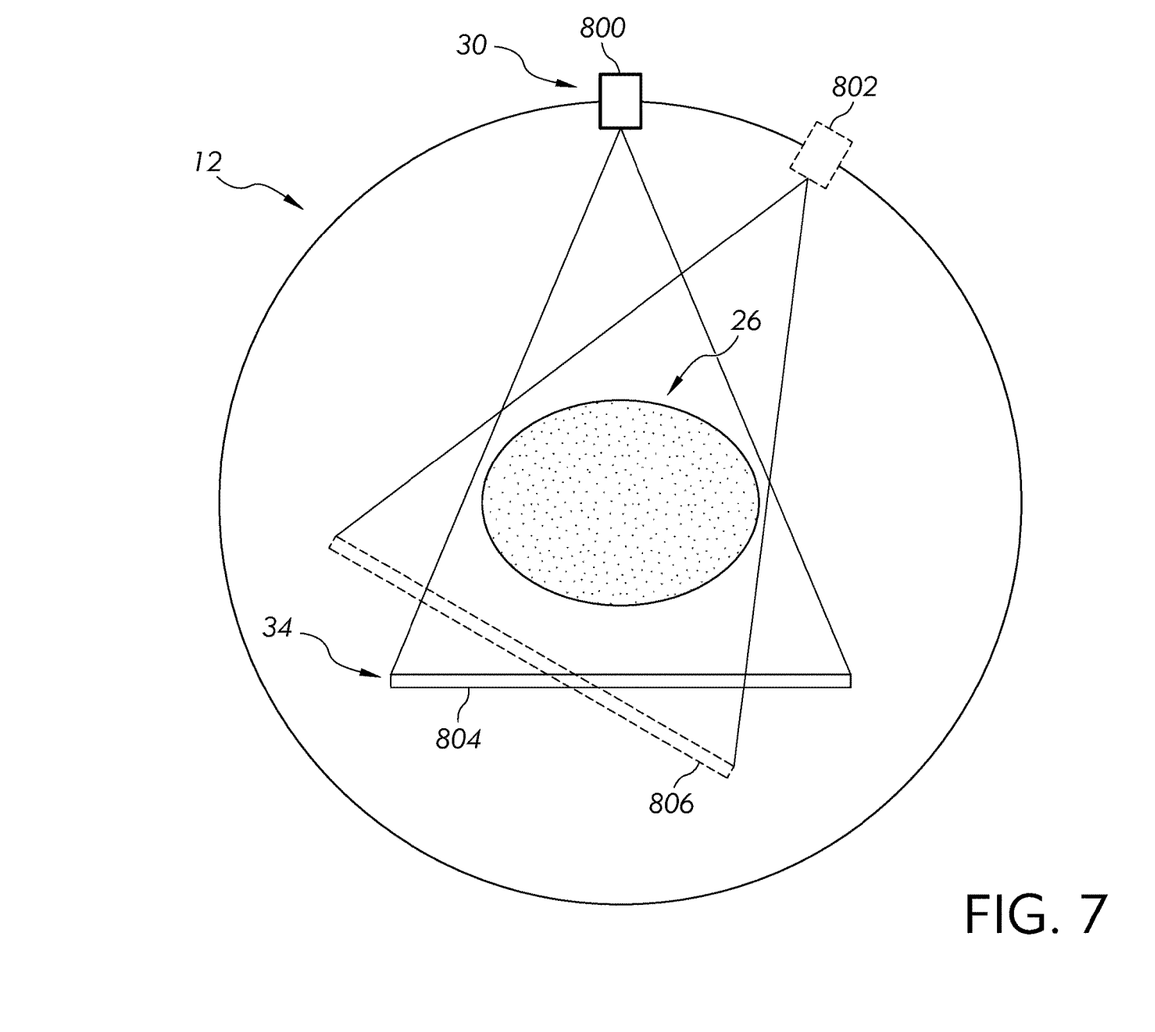
FIG. 7 is another example device configuration in accordance with one or more embodiments described herein.

FIG. 7 illustrates an example embodiment in which the dynamic gain setting is varied for high and low voltage pulses. In contrast to the embodiments described above, varying the dynamic gain setting can be implemented in configurations in which the tube current varies in addition to the voltage. Moreover, such embodiments can be used to select appropriate gain settings to reduce or even eliminate saturated rays in future scans.

In various embodiments, a first plurality of photons is emitted from a radiation source 30 at a first energy level and a second plurality of photons is emitted from the radiation source 30 at a second energy level. As illustrated in FIG. 7, a first pulse has a first voltage (e.g., 140 kV) and a first current (e.g., 80 mAs) when the radiation source 30 is at a first position 800, while a second pulse has a second voltage (e.g., 80 kV) and a second current (e.g., 120 mAs) when the radiation source 30 is at a second position 802. At least some of the first plurality of photons and at least some of the second plurality of photons are received at the x-ray detector 34. For example, when the radiation source 30 is at the first position 800, the x-ray detector 34 is at position 804, and when the radiation source 30 is at the second position 802, the x-ray detector is at position 806. It should be understood that the particular voltage and current for each pulse can vary depending on the particular embodiment.

Depending on the particular configuration, the energy received by the detector from the high energy pulses may be twice as much (or more) as that received by from the low energy pulses. Accordingly, a first detector gain (e.g., a high detector gain) can be selected for the first pulse configuration and a second detector gain (e.g., a low detector gain) can be selected for the second pulse configuration.

As a result of the photons received from each energy pulse, the x-ray detector outputs a signal indicative of the quantity of the photons received. For example, upon receipt of some of the first plurality of photons, the x-ray detector outputs a first signal indicative of a first quantity of the first plurality of photons received at the x-ray detector. In embodiments, the first signal is an amplification of the first quantity by a factor of the first gain level. Upon receipt of some of the second plurality of photons, the x-ray detector outputs a second signal indicative of a second quantity of the second plurality of photons received at the x-ray detector. In embodiments, the second signal is an amplification of the second quantity by a factor of the second gain level. Accordingly, the amplification of the quantity of received photons as a result of each pulse can be varied to generate a signal that can be utilized in image reconstruction. In particular, the first and second gain levels can be adjusted (e.g., increased or reduced depending on the values) to reduce or eliminate the number of saturated signals emitted during the next scan.

In various embodiments, a first gain level and a second gain level are selected to avoid saturation of a first signal corresponding to the first plurality of photons and a second signal corresponding to the second plurality of photons. Selection of each gain level can be based, for example, on saturation information obtained during previous scans (e.g., whether saturated signals were output for a particular pulse configuration during a previous scan, energy levels and gain levels utilized during the previous scan, etc.). For example, in an embodiment, the output of a saturated signal during a first scan can cause the controller to adjust the gain level for a subsequent scan. The adjusted gain level can be determined based on the energy level and gain level of the previous scan during output of the saturated signal and the energy level for the subsequent scan.

Although the disclosed technology has been shown and described with respect to a certain aspect, embodiment or embodiments, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, embodiment or embodiments of the disclosed technology. In addition, while a particular feature of the disclosed technology may have been described above with respect to only one or more of several illustrated aspects or embodiments, such feature may be combined with one or more other features of the other embodiments, as may be desired and advantageous for any given or particular application.

While the embodiments discussed herein have been related to the systems and methods discussed above, these embodiments are intended to be exemplary and are not intended to limit the applicability of these embodiments to only those discussions set forth herein. While the present invention has been illustrated by the description of embodiments thereof, and while the embodiments have been described in some detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general inventive concept.

The invention claimed is:

1. A method for correcting saturation in at least one saturated ray comprising:
   identifying a saturated ray corresponding to a first ray of a radiation source received at a radiation detector after passing through a reference point during a current view of the radiation detector and saturates a pixel of the radiation detector;
   identifying at least one non-saturated ray corresponding to a second ray of the radiation source received at the radiation detector after passing through the reference point during a previous view of the radiation detector and does not saturate a pixel of the radiation detector or a third ray of the radiation source received at the radiation detector after passing through the reference point during a next view of the radiation detector and does not saturate a pixel of the radiation detector, wherein:
   each of the previous view of the radiation detector and the next view of the radiation detector is adjacent to the current view; and
   the radiation source has a first energy for the current view and a second energy for the previous view and the next view, the second energy being different than the first energy; and
   responsive to the identifying, adjusting a value for the saturated ray based on a value of the at least one non-saturated ray.

2. The method according to claim 1, wherein the non-saturated ray is emitted during a current rotation of the radiation source.

3. The method according to claim 1, wherein the non-saturated ray is emitted during a rotation of the radiation source that is different from than a rotation of the radiation source during which the saturated ray is emitted.

4. The method according to claim 1, wherein the non-saturated ray corresponds to the second ray.

5. The method according to claim 1, wherein the non-saturated ray corresponds to the third ray.

6. The method according to claim 1, wherein the value of the saturated ray is adjusted based on a value of a non-saturated ray corresponding to the second ray and a value of a non-saturated ray corresponding to the third ray.

7. The method according to claim 1, wherein the adjusting the value of the saturated ray comprises adjusting the value of the saturated ray based on a value of the non-saturated ray and a value of a non-saturated ray adjacent to the saturated ray from the current view of the radiation detector.

8. A method for correcting saturation in at least one saturated ray comprising:
   identifying a saturated ray corresponding to a first ray of a radiation source received at a radiation detector after passing through a reference point during a current view of the radiation detector and saturates a pixel of the radiation detector;
   identifying at least one non-saturated ray corresponding to a second ray of the radiation source received at the radiation detector after passing through the reference point during a conjugate view and does not saturate a pixel of the radiation detector, wherein:
   the second ray is adjacent to a third ray, the third ray being rotated 180° with respect to the first ray; and
   responsive to the identifying, adjusting a value for the saturated ray based on a value of the at least one non-saturated ray.

9. The method according to claim 8, wherein the radiation source has a first energy for the current view and a second energy for the conjugate view, the second energy being different than the first energy.

10. The method according to claim 8, wherein the value of the saturated ray is adjusted based on a value of a non-saturated ray corresponding to the second ray and a value of a non-saturated ray in a frame of the saturated ray.

11. The method according to claim 8, wherein the value of the saturated ray is adjusted based on a value of a non-saturated ray corresponding to the second ray and a value of a non-saturated ray having a similar azimuth angle in a previous or next rotation as a rotation of the saturated ray.

* * * * *